Figure 1:
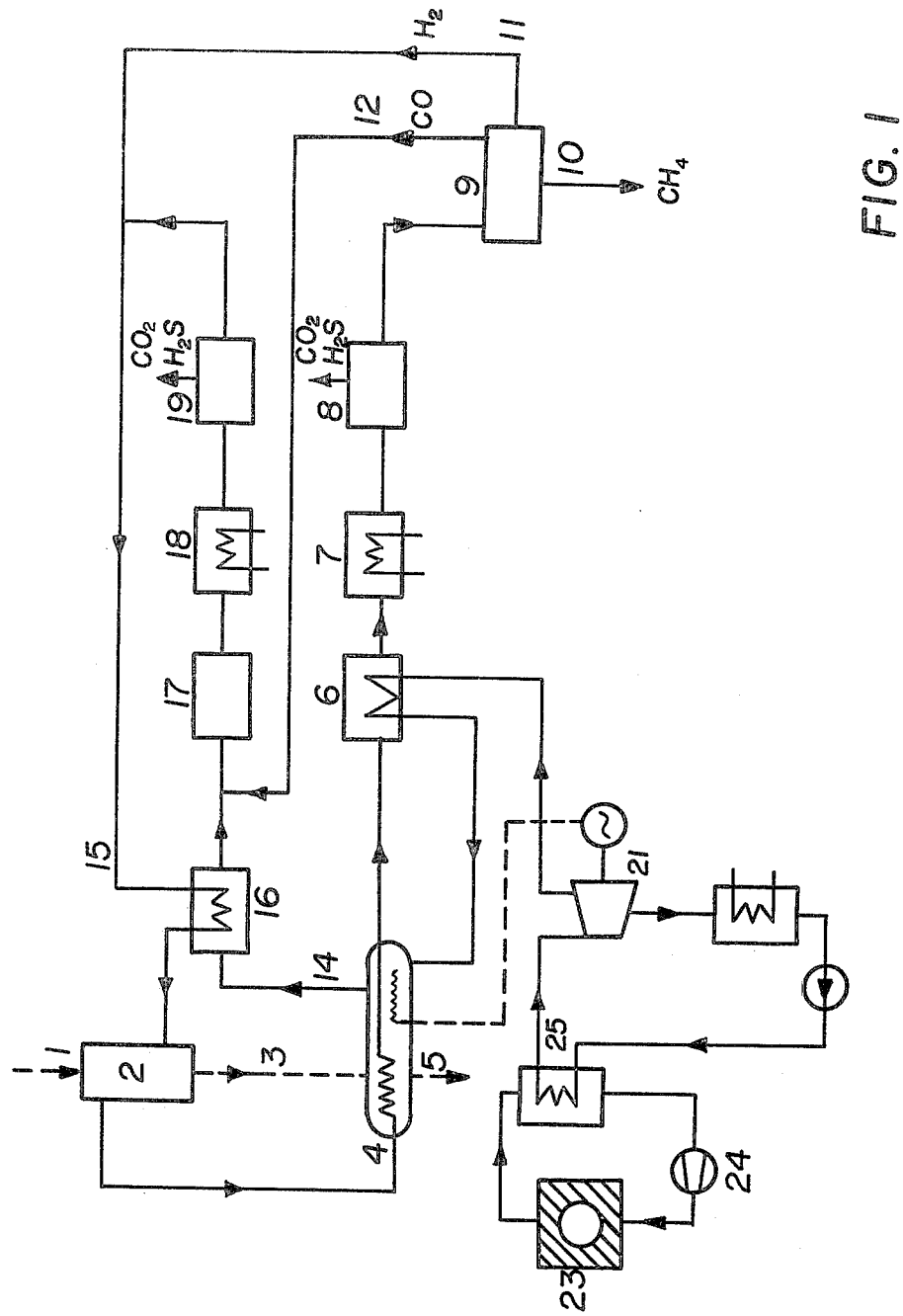

United States Patent [19]

Jäger et al.

[11] 4,337,067
[45] Jun. 29, 1982

[54] COAL GASIFICATION

[75] Inventors: Walter Jäger, Engelskirchen; Herbert von Waclawiczek, Bergisch Gladbach, both of Fed. Rep. of Germany

[73] Assignee: GHT Gesellschaft fur Hochtemperaturreaktor-Technik mbH, Bergisch Gladbach, Fed. Rep. of Germany

[21] Appl. No.: 195,195

[22] PCT Filed: Aug. 21, 1979

[86] PCT No.: PCT/DE79/00092
 § 371 Date: Apr. 29, 1980
 § 102(e) Date: Apr. 29, 1980

[87] PCT Pub. No.: WO80/00441
 PCT Pub. Date: Mar. 20, 1980

[30] Foreign Application Priority Data

Aug. 31, 1978 [DE] Fed. Rep. of Germany ....... 2837952

[51] Int. Cl.³ .............................. C10J 3/10; C10J 3/18
[52] U.S. Cl. ........................................ 48/202; 48/210; 252/373; 376/325
[58] Field of Search ............... 48/202, 210, 65, 197 R, 48/77; 176/39; 252/373; 422/199

[56] References Cited

U.S. PATENT DOCUMENTS

| | | | |
|---|---|---|---|
| 1,790,853 | 2/1931 | Casale | 422/199 |
| 2,631,930 | 3/1953 | Peters | 48/65 |
| 3,252,773 | 5/1966 | Solomon et al. | 48/202 |
| 4,005,045 | 1/1977 | Hoese | 176/39 |
| 4,095,959 | 6/1978 | Kunstle et al. | 48/77 |

FOREIGN PATENT DOCUMENTS 2553506 2/1977 Fed. Rep. of Germany ........ 48/210
2704465 8/1978 Fed. Rep. of Germany .

OTHER PUBLICATIONS

Oak Ridge National Laboratory Report TM-5242, Nov. 1976, p. 82, Spievak et al.
Vergasung Von Kohle mit Kernreaktorwarme, Juntgen et al., Chemie-Inglmieur-Technik, 1974, pp. 937-943.

Primary Examiner—Peter F. Kratz
Attorney, Agent, or Firm—Herbert L. Lerner; Laurence A. Greenberg

[57] ABSTRACT

Method for generating methane or synthesis gas from carbon-containing materials, e.g. coal, by reacting part of the carbon with hydrogen in a hydrogenating gasifier to produce a methane containing gas, and reacting the residual carbon with steam in a steam gasifier to produce a raw gas containing synthesis gas. Features are:
 (a) The steam gasifier is heated with the raw gas leaving the hydrogenating gasifier.
 (b) The hydrogen gas entering the hydrogenating gasifier is heated with the raw gas leaving the steam gasifier.
 (c) The output stage of the steam gasifier is heated electrically.
 (d) The entire nuclear heat is given off to a steam loop.

In addition a methane cracking furnace may be provided with the following features:
 (a) The methane cracking furnace is heated electrically in the upper temperature range.
 (b) The raw gas leaving the methane cracking furnace serves for heating the entering methane.

2 Claims, 2 Drawing Figures

COAL GASIFICATION

The present invention relates to a plant for generating methane or synthesis gas from carbon-containing materials, especially by utilizing nuclear energy. In this process, a first part of the carbon is reacted with hydrogen to methane in a hydrogenating gasifier and a second part of the carbon is reacted with steam to synthesis gas in a steam gasifier. These plants furnish either methane ($CH_4$) or synthesis gas as a mixture of $H_2$ and CO. This plant is suitable particularly for coal grades which do not react readily, such as hard coal.

Figure 2:
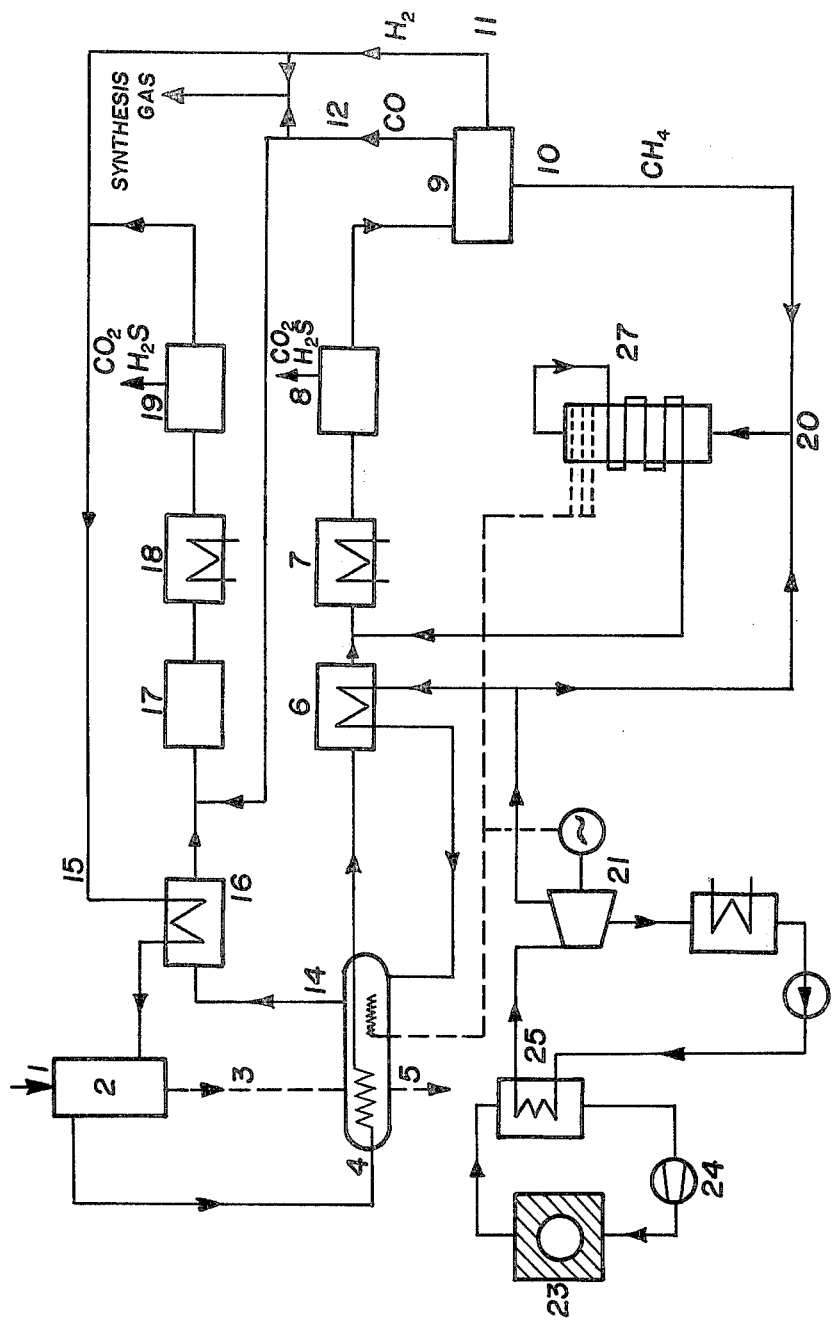

In "Chemie-Ingenieur-Technik" 1974, page 938, especially in FIG. 1 as well as page 941, especially FIG. 2, a schematic process is described in each for producing methane via steam gasification of coal. On page 937, new processes of gasification of coal to methane by hydrogenation are mentioned. Both processes, however, have a considerable disadvantage. With gasification by hydrogenation, complete reaction of the coal is not attainable, because a long dwelling time of the carbon is required to get more complete reaction and for practical purposes the gasifier has limited dimensions. The residual coke obtained in the hydrogenating-gasification contains, in addition to the ash, about 30 to 45% of the carbon charged-in. In the steam gasification, on the other hand, the charged-in carbon can be gasified almost without residue. This process takes place only at high temperatures (bituminous coal, 790° C.; lignite, 630° to 660° C.), and only the upper temperature range of the heat released in the reactor can be utilized for the gasification. In the case of a pure steam gasification process, the residual heat can essentially only be used for generating steam and therefore for generating power because only a small part of this steam can be used in the process.

In the report ORNL/TM-5242 (Oak Ridge National Laboratory, November 1976) page 82, a plant is shown in which carbon is reacted to methane by means of nuclear heat. The coal is first dried, then gasified by hydrogenation, and the residual coke is converted in a steam gasifier into synthesis gas. Part of the methane produced with added hot steam is reacted in a methane cracking furnace (called a reformer there) to synthesis gas. This arrangement, however, has the following further disadvantages: The process heat exchangers arranged in a primary or also in a secondary helium loop are very expensive. Heilum carrying piping and apparatus place increased requirements on the tightness which is necessary to prevent undesired substances from penetrating into the primary loop and either have corrosive effects there, or cause undesirable deposits which become activated in such a manner that they cause trouble at other places. In addition, all process heat exchangers heated with pure helium have the disadvantage that helium, being a single-atom gas, gives off no radiation heat, which is disadvantageous particularly at the high temperatures here. Consequently, the velocity of the helium would have to be increased in order to increase the heat transfer through convection. This increases the pressure loss, or else the heating surfaces would have to be enlarged.

In German Published Non-Prosecuted Application No. 25 53 506.2, a plant for producing methane or synthesis gas from carbon-containing materials by means of a nuclear reactor is described, wherein part of the carbon-containing material is converted into synthesis gas, with the addition of steam and at high temperature, in a steam gasifier. This plant has two reactor cooling loops; in a first cooling loop is arranged the steam gasifier and in a second cooling loop is arranged a reformer known per se in which part of the methane produced is cracked at high temperature to hydrogen, which latter is used for the hydrogenating-gasification of another part of the carbon-containing material. This two-stage gasification combines in an advantageous manner the following requirements: low coal consumption, complete gasification of the coal, inclusion of the entire nuclear reactor heat into the gasification process so that almost no power needs to be given off to the outside, and a high overall efficiency. A disadvantage is still that the heating required for the steam gasifier must be made available at high temperature either directly or via an intermediate loop by the nuclear-heated helium. This helium would have to have a temperature of about 900° to 950° C. and the parts of the plant between the nuclear reactor and the gasification plant must be suitable for this high temperature. A secondary helium loop which transfers the heat of the nuclear reactor from the primary loop thereof to the gasification plant is accompanied by considerable cost and also with additional losses. The close coupling between the nuclear reactor and the gasification plant necessitates considerable costs for safety and makes the operation of the overall plant more difficult.

The object of the present invention is to provide a method in a plant for generating methane or synthesis gas from carbon-containing-materials, which avoids the described disadvantages to a large extent and is largely decoupled from a nuclear reactor plant, so that disturbances in one part of the overall plant cannot have an immediate effect on the other part of the plant. In addition, such a plant should not require considerable amounts of electric power from an external source nor require disposal of considerable power to an external source. At the same time, the process temperatures are raised to about 1000° C. through electric heating, which at the present time cannot be realized with purely nuclear heating processes. At this temperature in the methane cracking furnace, the chemical processes take place completely so that the product gas contains only small percentages of non-reacted methane and the cost for purification and dissociation apparatus becomes smaller. In the last stage of the steam gasifier, the high temperature is to bring about a far-reaching conversion of the carbon. As a solution to this problem, a plant is proposed for generating methane or synthesis gas from carbon containing materials, utilizing nuclear energy; in this process, a first part of the carbon is reacted with hydrogen to methane in a hydrogenating gasifier and a second part of the carbon is reacted with steam in a steam gasifier to synthesis gas. This plant has the following features:

(a) The steam gasifier is heated with the raw gas leaving the hydrogenating gasifier.
(b) The hydrogen gas entering the hydrogenating gasifier is heated with the raw gas leaving the steam gasifier.
(c) The output stage of the steam gasifier is heated electrically.
(d) The entire nuclear heat is given off to a steam loop.Since the raw gases leave the hydrogenating and steam gasifier at a very high temperature and it is uneconomical to utilize this high temperature, as heretofore, only for preheating the entering raw gas or only for generating steam, a high overall efficiency of the plant can be expected with this arrangement. The requirements as to tightness of a heat exchanger, particularly in the area of the steam gasifier, are considerably less stringent if only process gases are carried on both sides and not a reactor coolant. However, the most important advantage of this plant is that the gasification plant is largely decoupled from its energy supply, particularly a nuclear reactor plant. Nuclear power plants are arranged for safety reasons in a so-called containment which encloses all radioactive loops and which can be closed off completely in case of an accident. Through this containment may pass piping for water or steam. The continuous charging with large quantities of solids and moving the residual coke or the ash through locks, would however, be accompanied by considerable costs. In addition, the gasifier can be operated, independently of the reactor, at its optimal operating pressure, i.e., for instance at 80 bar.

This plant has as the sole coupling between the gasification plant and the nuclear reactor a steam generator which can be arranged at low expense of technical means within the containment and can be heated by the primary medium also without a secondary cooling loop. A methane cracking furnace customary in such plants can be omitted if methane is to be produced. If the steam gasifier is heated in part electrically, the nuclear reactor which may be a high-temperature reactor as well as a pressurized-water reactor, can be separated spatially from the gasification plant. The only lines which must pass through the containment of the nuclear reactor for utilization of reactor energy for the plant in accordance with the invention are water or steam lines, the technology of which belongs to the secure state of the art in nuclear reactor plants. The transmission of power from the nuclear reactor via steam generators, turbines and generators down to the electric heating is naturally connected with lower efficiency as compared to direct heating. However, since only part of the nuclear energy is used for generating electric power and a large part of the nuclear energy is introduced into the gasification plant as process steam without appreciable losses, the overall plant has a high efficiency with a substantially lower investment cost. Under these circumstances, one can even afford to make the nuclear energy available, for instance, with a pressurized-water-reactor. The proposed electric heating is particularly well suited for gasification of the residual coke, since the latter already contains large percentages of ash and accordingly reacts sluggishly.

The plant serves for producing synthesis gas and therefore includes a methane cracking furnace which, however, deviating from the past, is heated electrically. The plant with a methane cracking furnace has the following features:

(a) The methane cracking furnace is heated electrically in the upper temperature range.

(b) The raw gas leaving the methane cracking furnace serves for heating the entering methane. Here, a special operating advantage of electric heating over direct heating with helium manifests itself. The necessary change of catalyst can be carried out without shutting down the reactor because in plants of this kind, numerous parallel connected cracking furnaces are in probability available, of which always one can be separated from the plant and serviced without interfering with the rest of the plant. In addition, the nuclear reactor, the gasifier and the cracking furnace can be operated independently of each other always at the optimum pressure.

FIG. 1 illustrates as an example of the invention, a schematic method of carrying out the operation. The milled and dried coal is fed to the hydrogenating-gasifier 2 and is gasified there with hydrogenation. The residual coke obtained there is taken via the path 3 to the steam gasifier 4, the output stage of which is heated electrically, and is gasified further. The residue obtained there consists of ash with a small percentage of carbon and is drawn off at 5. The raw gas leaving hydrogenating-gasifier 2 gives off part of its heat in the upper temperature range in the steam gasifier 4, and thereafter gives off its heat at its lower temperature range in the process steam superheater 6 and in the steam generator 7. After cooling down, the raw gas is freed at 8 of dust and tar as well as of carbon dioxide and hydrogen sulfide in a scrubber. In the low-temperature decomposition or separation plant 9, the purified gas is separated into a methane fraction 10, a hydrogen fraction 11 and a carbon monoxide fraction 12. The methane is fed to a gas network. The hydrogenation gas leaving the steam gasifier 4 on the path 14 gives off in the heat exchanger 16 part of its heat to the hydrogenation gas 15 which is to be fed to the hydrogenating-gasifier 2. The carbon monoxide contained in the hydrogenation gas together with steam is converted in the conversion plant 17 into hydrogen and carbon dioxide. Thereupon, the hydrogenation gas is further cooled down in the waste-heat boiler 18, process steam being generated. After carbon dioxide and hydrogen sulfide have been removed in the gas scrubber 19, the so purified gas is preheated with the hydrogen given off in the low-temperature separation plant 9 on the path 15 in the heat exchanger 16 and the preheated gases introduce into the hydrogenating-gasifier 2 wherein it converts a large part of the carbon therein into methane. The entire thermal energy is made available by a nuclear reactor 23, the closed primary loop of which is operated by a blower or a pump 24 and which gives off its usable heat to a steam generator 25.

FIG. 2 shows another example of the invention in the schematic form of a coal gasification plant, which essentially serves for generating synthesis gas and therefore comprises a methane cracking furnace. In contrast to the plant already described in FIG. 1, a methane cracking furnace 27 is provided here, which furnace is heated in its upper temperature range with electric current from the steam turbine plant 21 and which is supplied at 20 with a mixture of methane and steam. The discharged cracked raw gas serves cross-counter flow-wise for heating the entering methane-steam mixture and is fed to the raw gas leaving the steam gasifier between the process steam heater 6 and the process steam generator 7. Likewise different from FIG. 1, methane is not given off to the outside in FIG. 2, but the methane is sent to the cracking furnace 27 and the reaction products therefrom discharged as synthesis gas as a mixture of the hydrogen stream 11 and the carbon monoxide stream 12.

The following numerical examples refer to a coal gasification plant according to the invention which is heated by a nuclear reactor.

EXAMPLES

| | |
|---|---|
| Thermal reactor output: | 1 500 MW |
| Type of Coal: Long-flame gas coal with 38% volatile components | |
| Calorific value of the methane produced | 40,693 KJ/$m_N^3$ |
| Composition: 95% $CH_4$ and 5% $C_2H_6$ | |
| 60% max. of the coal are gasified by hydrogenation. | |

EXAMPLE 1

| High-temperature reactor with electrically heated cracking furnace | | |
|---|---|---|
| Coal throughput: | | 525 t/h |
| Methane production: | | 379 . $10^3$ $m_N^3$/h |
| Power consumption: | Gasifier | 147 MW |
| | Cracking furnace | 74 MW |
| | Gas plant | 259 MW |
| Thermal reactor output for process steam | | 115 MW |

EXAMPLE 2

| Light-water reactor with electrically heated cracking furnace | | |
|---|---|---|
| Coal throughput: | | 442 t/h |
| Methane production: | | 319 . $10^3$ $m_N^3$/h |
| Power consumption: | Gasifier | 124 MW |
| | Cracking furnace | 62 MW |
| | Gas plant | 216 MW |
| Thermal reactor output for process steam | | 283 MW |

EXAMPLE 3

| Light-water reactor without methane cracking furnace | | |
|---|---|---|
| Coal throughput: | | 452 t/h |
| Methane Production: | | 327 . $10^3$ $m_N^3$/h |
| Power consumption: | Gasifier | 164 MW |
| | Gas plant | 221 MW |
| Thermal reactor output for process steam | | 333 MW |

In all examples, the output stage of the steam gasifier is heated electrically and no power is given to the outside.

We claim:

1. Method for generating methane or synthesis gas from carbon-containing materials utilizing nuclear energy which comprises subjecting the carbon-containing material to hydrogenation in a hydrogenation-gasifier to convert part of the carbon in the carbon-containing material to gaseous constituents containing methane which are released from the hydrogenation-gasifier, introducing a hydrogen-containing gas into the hydrogenation-gasifier, passing residual unvaporized carbonaceous material from the hydrogenation-gasifier to convert the carbon in the residual carbonaceous material to gases containing synthesis gas which are released from an outlet of the steam gasifier, heating the steam gasifier by heat exchange with the gaseous constituents released from the hydrogenation-gasifier, electrically heating the steam gasifier at its output stage, heating the hydrogen containing gas entering the hydrogenation-gasifier by heat exchange with the gases containing synthesis gas released from the steam gasifier, generating heat in a nuclear reactor, transferring said heat to a steam generator as a sole coupling between the above gasification operation and the nuclear reactor, and utilizing steam from said steam generator for process steam and for generating electricity for said electrically heating in the above operation for gasifying carbon-containing material.

2. Method for producing synthesis gas according to claim 1, wherein methane generated from the carbon-containing materials together with steam is heated in a methane cracking furnace which is heated electrically in the upper temperature range, and wherein the raw gas leaving the methane cracking furnace heats the entering methane by passing in indirect heat exchange with the entering methane.

* * * * *